US005665564A

United States Patent [19]

Caruso et al.

[11] Patent Number: 5,665,564
[45] Date of Patent: Sep. 9, 1997

[54] ISOLATION AND CHARACTERISATION OF GENES RESISTANT TO ANTHRACYCLINE ANTIBIOTICS

[75] Inventors: Marinella Caruso; Anna Luisa Colombo, both of Milan; Luisa Garofano, Monza; Francesca Torti, Milan; Guiseppe Zanella, Buccinasco, all of Italy

[73] Assignee: Pharmacia & Upjohn S.p.A., Milan, Italy

[21] Appl. No.: 103,319

[22] Filed: Aug. 9, 1993

Related U.S. Application Data

[63] Continuation of Ser. No. 960,303, Oct. 13, 1992, abandoned, which is a continuation of Ser. No. 790,027, Nov. 6, 1991, abandoned, which is a continuation of Ser. No. 458,677, filed as PCT/EP89/00588 on May 26, 1989, abandoned.

[30] Foreign Application Priority Data

May 27, 1988 [GB] United Kingdom .................. 8812697

[51] Int. Cl.$^6$ .......................... C12N 5/00; C12N 15/00; C07H 17/00
[52] U.S. Cl. ............... 435/69.1; 435/320.1; 435/252.35; 435/91.41; 435/78; 536/23.7
[58] Field of Search ...................... 435/64, 69.1, 78, 435/320.1, 240.2, 172.1, 172.2, 172.3, 34, 252.35

[56] References Cited

FOREIGN PATENT DOCUMENTS

| 0173327 | 3/1986 | European Pat. Off. . |
| 0204549 | 12/1986 | European Pat. Off. . |

OTHER PUBLICATIONS

Applied and Environmental Microbiology (1986) vol. 51 (1), pp. 126–131.
PNAS (1987), vol. 84, pp. 9261–9264, 3004–3008.
J. Gen. Appl. Microbiol. (1985), vol. 31, pp. 231–241.
Experientia, vol. 38, 1982 (Basel, CH), N. Crespi-Perellino et al.: "Bio-synthetic relationships among daunorubicin, doxorubicon and 13–dihydro–daunorubicin in Streptomyces peucetius" pp. 1455–1456.
Abstracts of the Annual Meeting of the American Society for Microbiology, 88th Annual Meeting, 8–13 May 1988, Miami Beach, FL., American Soc. For Microbiology (US) K.J. Stutzman–Engwall et al.: "Cloning and identification of genes involved in daunorubicin production in Streptomyces peucetius", see page 261, abstract 0–2.

194th American Chemical Society National Meeting, 30 Aug.—4 Sep. 1987, New Orleans, Louisiana, US Abstr. Pap. Am. Chem. Soc. 194(0) 1987 Medi 5 (US) C.R. Hutchinson et al.: "Possibilities for the development of new antitumor drugs by genetic engineering of anthracycline", see abstract.

Katz et al., Journal of General Microbiology, vol. 129, pp. 2703–2714 (1983).

Stutzman–Engwall et al., Proc. Natl. Acad. Sci. USA, vol. 86, pp. 3135–3139, (1989).

Nature, vol 325, 26 Feb. 1987, F. Malpartida et al.: "Homology between Streptomyces genes coding for synthesis of different polyketides used to clone antibiotic byosynthetic genes" pp. 818–821, see figures 1,2; p. 819.

Mol. Gen. Genet., vol. 205, 1986, Springer–Verlag, T. Murakami et al.: "The bialaphos biosynthesis genes of Streptomyces hygroscopicus: Molecular cloning and characterization of the gene cluster", pp. 42–50.

Chemical Abstracts, vol. 104, 1986, (columbus, Ohio, US), J.S. Lampel et al.: "Transformation and transfection of anthracycline–producing streptomycetes", p. 178, resume 103498p & Appl. environ, Microbiol. 1986, 51(1), 126–31.

Journal of Bacteriology, vol. 151, No. 2, (US), C.J. Thompson et al.: "Bio–chemical characterization of resistance determinants cloned from antibiotic–producing streptomycetes", pp. 678–685.

The Journal of Antibiotics, vol. 59, No. 1, Jan. 1986, R. Crameri et al.: "Increased production of aminoglycosides associated with amplified antibiotic resistance genes", p. 128.

Primary Examiner—Vasu S. Jagannathan
Assistant Examiner—Karen Cochrane Carlson
Attorney, Agent, or Firm—Oblon, Spivak, McClelland, Maier & Neustadt, P.C.

[57] ABSTRACT

Doxorubicin resistance can be conferred on a host by transforming the host with a recombinant vector comprising a DNA having the configuration of restriction sites shown in FIGS. 1 or 2 of the accompanying drawings or a restriction fragment derived therefrom containing a gene coding for doxorubicin resistance.

17 Claims, 1 Drawing Sheet

ISOLATION AND CHARACTERISATION OF GENES RESISTANT TO ANTHRACYCLINE ANTIBIOTICS

This application is a Continuation of application Ser. No. 07/960,303, filed Oct 13, 1992, abandoned, which is a Continuation of Ser. No. 07/790,027, filed Nov. 6, 1991, abandoned, which is a Continuation of Ser. No. 07/458,677, filed Mar. 27, 1990, abandoned, which was filed as International Application No. PCT/EP89/00588 on May 26, 1989.

This invention relates to DNA fragments comprising genes conferring resistance to anthracycline antibiotics, to recombinant vectors comprising such DNA fragments and to hosts transformed with the vectors.

BACKGROUND OF THE INVENTION

The anthracyclines of the daunorubicin group, such as doxorubicin, carminomycin and aclavinomycin, are among the most widely employed agents in antitumoral therapy. They are polyketides produced by various strains of Streptomyces (*S. peucetius, S. coeruleorubidus, S. galilaeus, S. griseus, S. griseoruber, S. viridochromogenes* and *S. bifurcus*).

Doxorubicin is only produced by *S. peucetius* var. *caesius*. The type strain *S. peucetius* var. *caesius* IMRU 3920 (hereinafter abbreviated to "*S. peucetius* 39.20") is publically available and is described in U.S. Pat. No. 3,590,028. *S. peucetius* 3920 has been deposited at the Institute of Microbiology of the Rutgers University, US, receiving the index number IMRU 3920. This strain and its mutants obtained by classical mutagenic treatments are resistant to high levels of doxorubicin.

The study of the mechanisms involved in the resistance to these substances is crucial for two main reasons:

a) There are many examples in which the genes involved in the biosynthesis of secondary metabolites are all clustered together with at least one resistance gene: for example oxytetracycline (Rhodes P. M., Hunter I S., Friend E. J. and Warren M., 1984, Trans Biochem Soc 12, 586–587), erythromycin (Stanzak R., Matsushima P., Baltz R. H. and Rao R. N., Biotechnology vol 4, March 1986, 229–232), tylosin (Fayerman J. T., Biotechnology vol 4, September 1986, 786–789) and tetracenomycin (Motamedi H., Hutchinson C. R., Proc Natl Acad Sci U.S.A., vol 84, 4445–4449, 1987). Cloning the biosynthetic genes can be useful with a view to altering pathways to produce different molecules or to overcome bottlenecks present in the biosynthesis routes thus augmenting the productivity of the strain.

b) The resistance itself can be implied in the regulatory mechanisms so that changing the resistance levels (i.e. augmenting the gene dosage) the productivity of the strain can be improved. This is an old idea usually performed via the classical methods of mutagenesis and random screening, but renewed by the utilisation of rDNA methods (Craveri R. and Davies J. E., The Journal of Antibiotics, January 1986, 128–135).

SUMMARY OF THE INVENTION

We have now isolated two DNA segments which incorporate doxorubicin resistance genes. Accordingly, the present invention provides DNA having the configuration of restriction sites shown in FIGS. 1 or 2 of the accompanying drawings or a restriction fragment derived therefrom containing a gene coding for doxorubicin resistance. For convenience, the DNA segments shown in FIGS. 1 and 2 are called here insert DNA. The invention also provides:

recombinant vectors which are capable of transforming a host cell and which contain an insert DNA or a restriction fragment derived therefrom containing a doxorubicin resistance gene; and host cells transformed with such vectors.

BRIEF DESCRIPTION OF THE DRAWINGS

In more detail, in the accompanying drawings.

Figure 1:
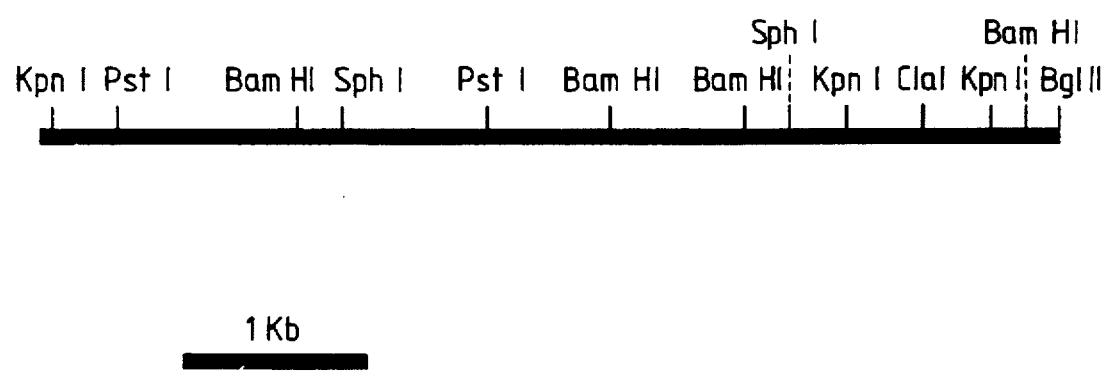
FIG. 1 is the restriction map analysis of a first DNA of the invention. This is an insert in recombinant plasmid FICE 1 (Rec 1). The insert has Sau3AI ends and was inserted into the BglII site of pIJ702. One BglII site was reconstituted after ligation.
Figure 2:
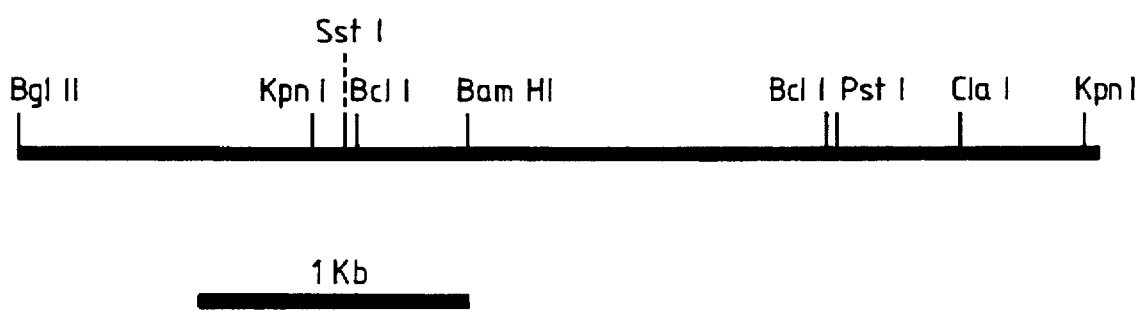
FIG. 2 is the restriction map analysis of a second DNA of the invention. This is an insert in recombinant plasmid FICE 2 (Rec 2). The insert has Sau3AI ends and was inserted into the BglII site of pIJ702. One BglII site was reconstituted after ligation.

The maps shown in FIGS. 1 and 2 do not necessarily provide an exhaustive listing of all restriction sites present in each DNA segment. However, the reported sites are sufficient for an unambiguous recognition of the segments.

DESCRIPTION OF THE PREFERRED EMBODIMENTS

The insert DNAs and restriction fragments of the invention contain a gene coding for doxorubicin resistance. For such a gene to be expressed, the DNA may carry its own transcription control sequence and, in particular, its own promoter which is operably connected to the gene and which is recognised by a host cell RNA polymerase. Alternatively, the insert DNA or restriction fragment may be ligated to another transcription control sequence in the correct fashion or cloned into a vector at a restriction site appropriately located neighbouring a transcription control sequence in the vector.

An insert DNA or restriction fragment carrying a doxorubicin resistance gene may be cloned into a recombinant DNA cloning vector. Any autonomously replicating and/or integrating agent comprising a DNA molecule to which one or more additional DNA segments can be added may be used. Typically, however, the vector is a plasmid. A preferred plasmid is the high copy number plasmid pIJ702 (Katz et al, J Gen Microbiol 1983 129 2703–2714). Any suitable technique may be used to insert the insert DNA or restriction fragment thereof into the vector. Insertion can be achieved by ligating the DNA into a linearised vector at an appropriate restriction site. For this, direct combination of sticky ends or homopolymer tailing or the use of a linker or adapter molecule may be employed.

The recombinant vector is used to transform a suitable host cell, typically cells that would benefit from being able to exhibit doxorubicin resistance. The host cells may be ones which are doxorubicin-sensitive, i.e. cannot grow in the presence of doxorubicin or ones which are doxorubicin-resistant but would benefit from greater resistance to doxorubicin. The host may be a microorganism. Strains of *S peucetius*, more particularly *S peucetius* var. *caesius*, which produce doxorubicin and other strains of Streptomyces which produce anthracyclines may therefore be transformed. Resistance, or greater resistance, to doxorubicin may enable more doxorubicin to be produced by cells of such a strain. Tolerance of greater concentrations of doxorubicin may be achieved. Transformants of strains of *S peucetius* are typically obtained by protoplast transformation. Doxorubicin can thus be obtained by culturing a transformed strain of *S peucetius* and recovering the doxorubicin thus-produced.

The insert DNAs are obtained from the genomic DNA of *S peucetius* M76. *S peucetius* M76 is a mutant of *S peucetius* 3920 which is able to convert daunorubicin to doxorubicin at high levels. *S peucetius* M76 was deposited at the Deutsche Sammlung yon Mikroorganismen (DSM), Federal Republic of Germany on 11 May 1988 under accession number D.S.M. 4592. A strain derived therefrom from *S peucetius* M76 may also be used, which typically will also be able to convert daunorubicin to doxorubicin. Insert DNAs may therefore be obtained by:

(a) preparing a library of the genomic DNA of *S peucetius* M76 or a strain derived therefrom;

(b) screening the library for doxorubicin resistance;

(c) obtaining an insert DNA from a recombinant vector which forms part of the library and which has been screened as positive for doxorubicin resistance; and (d) optionally, obtaining from the insert DNA a restriction fragment which contains a gene coding for doxorubicin resistance.

The library may be prepared in step (a) by partially digesting the genomic DNA of *S peucetius* M76 or a strain derived therefrom. The restriction enzyme MboI is preferably used. The fragments thus obtained can be size-fractionated. Fragments of from 4 to 6 Kb in size are preferred. These fragments are ligated into a linearised vector such as pIJ702. Host cells are transformed with the ligation mixture. Typically, the host cells are doxorubicin-sensitive, for example sensitive to 50 µg or less or, preferably 30 µg or less of doxorubicin per ml. For example, *S lividans* TK 23 protoplasts may be transformed.

In step (b), the transformants thus-obtained are screened for doxorubicin resistance. Clones doxorubicin-resistant are identified by growth in a medium containing doxorubicin. Such clones are isolated and recombinant vectors contained therein are extracted. On digestion of the recombinant vectors with suitable restriction enzymes in step (c), the *S peucetius* M76 DNA inserted into each vector may be identified, sized and mapped. In this way, it may be checked that the vector contains an insert DNA of the invention.

Further, two or more overlapping inserts may be isolated which are wholly or partly embraced within the DNA of the invention. These may be fused together by cleavage at a common restriction site and subsequent ligation to obtain a DNA of the invention, pared in length using appropriate restriction enzymes if necessary. Restriction fragments of an insert DNA which contains a gene encoding for doxorubicin resistance may be obtained in step (d) also by cleaving an insert DNA with an appropriate restriction enzyme.

Finally, DNA of the invention may be mutated in a way which does not affect its ability to confer doxorubicin resistance. This can be achieved via site-directed mutagenesis for example. Such mutated DNA also forms part of the invention.

The following Example illustrates the invention. In the Example $Ts^R$, $Doxo^R$ and $Doxo^S$ denote the thiostrepton-resistant, the doxorubicin-resistant and the doxorubicin-sensitive phenotypes respectively.

EXAMPLE

1. Materials and Methods

Bacterial Strains and Plasmids

*Streptomyces peucetius* M76, a filamentous streptomycete producing daunorubicin and doxorubicin and resistant to doxorubicin (MIC 250 µg/ml), and some biosynthetic routants sensitive to doxorubicin; *S. lividans* TK 23 sensitive to doxorubicin.

Plasmid pIJ702 a high copy number was obtained from the John Innes Culture Collection, Norwich, GB.

Media and Buffers

TSB contained 30 g of tryptic soy broth (DIFCO) per litre of distilled water; YEME contained 5 g of yeast extract (DIFCO), 10 g of malt extract (DIFCO), 340 g of sucrose, 5 mM $MgCl_2.6H_2O$ and variable glycine concentrations per litre of distilled water.

The regeneration medium R2YE was as described by Chater K. F., Hopwood D. A., Kieser T. and Thompson C. J. (1982) "Gene cloning in Streptomyces", 69–95 in P. H. Hofschneider and W. Goebbel (ed) "Gene Cloning in Organisms other than *E. coli*", Springer-Verlag, Ber. lin. The medium was prepared with the following composition per litre:

| sucrose | 103 g | trace elements mix | 2 ml |
|---|---|---|---|
| 2.5% $K_2SO_4$ | 10 ml | 0.5% $KH_2PO_4$ | 10 ml |
| $MgCl_2.6H_2O$ | 10.1 g | 1M $CaCl_2$ | 20 ml |
| glucose | 10 g | proline | 3 g |
| casaminoacids | 0.1 g | 0.25M TES pH 7.2 | 100 ml |
| agar | 22 g | 10% yeast extract | 50 ml |

Medium P was as described by Baltz R. H., J Gen Microbiol 107:93–102 (1978).

Streptomycetes were maintained on solid medium described in U.S. Pat. No. 3,590,028, Example 2.

Growth Conditions

For liquid cultures both Streptomyces species were grown in 50 ml of YEME+TSB (1:1) at 28° C. on a rotary shaker at 280 rpm. The growth medium was inoculated with homogenised mycelia. Homogenisation was obtained by vortexing mycelia in a tube containing glass beads.

Protoplast Transformation

Mycelia from 35 ml of liquid culture (supplemented with 0.5% glycine) were recovered by centrifugation (10 min, 1500×g), washed twice with 10.3% sucrose, resuspended in 10 ml of P medium containing 1 mg/ml of lysozyme (SIGMA) and incubated for 60 minutes at 30° C. with reciprocal shaking (280 rpm). After protoplast formation the suspension was filtered through cotton, washed once with medium P and resuspended in 1 ml of medium P. Usually $10^8$ protoplasts were obtained.

For each transformation 200 ul of medium P containing about $2\times10^7$ protoplasts were mixed with 10 ul of the desired amount of DNA in TE (Tris-HCl 10 mM, EDTA 1 mM pH 8.0), and with 800 ul of 25% polyethylene glycol (PEG) 1000 in medium P. 1 Minute after the addition of PEG solution, transformation was terminated by the addition of 5 ml of medium P. Protoplasts were pelletted by centrifugation, resuspended in 1 ml of P and plated on R2YE. After incubation for 24 hours at 28° C. transformants were selected by flooding the plates with 3 ml soft NA (8 g of DIFCO nutrient broth and 5 g of agar per litre) containing the appropriate antibiotic. The number of transformants was about $1\times10^4$–$1\times10^7$ per mcg of DNA, according to the strains utilised.

Isolation of Plasmid and Genomic DNA

Isolation of plasmid and genomic DNA from streptomycetes was performed using techniques described by Hepwood D. A. et al (1985) "Genetic Manipulation of Streptomyces—A Laboratory Manual" The John Innes Foundation.

Preparation of S. peucetius M76 Genomic Library

All restriction enzymes, calf thymus alkaline phosphatase and T4 ligase were obtained from BRL (Bethesda, Md.) and used according to the manufacturer's instructions. S. peucetius M76 genomic DNA was partially digested with MboI, and fragments ranging between 4 and 6 Kb in size recovered by electroelution from agarose gel. These fragments were ligated to pIJ702 linearised with BglII and phosphatase treated. The ligation mixture was used to transform S lividans TK 23 protoplasts sensitive to 30 mcg/ml of doxorubicin.

2. Results

Cloning of DNA Fragments Which Confer Resistance to Doxorubicin in Sensitive Streptomyces Strains Partially MboI digested S. peucetius M76 genomic DNA was inserted into the BglII site of pIJ702. The ligation mix was used to transform S lividans TK 23 protoplasts. Transformants were selected for Thiostrepton resistance and white colour, indicating insertional inactivation of the melanin gene of pIJ702.

Thiostrepton-resistant white colonies were then screened for resistance to doxorubicin (100 µg/ml). They were plated on R2YE medium, incubated at 28° C. for 24 hours with 3 ml of soft NA containing 500 µg/ml of doxorubicin; two clones $Ts^R$ and $Doxo^R$ were thus identified.

Extraction of plasmid DNA from these two clones revealed the presence of inserts of 5.7 kb and 4.4 kb in length. The two recombinant plasmids, named respectively FICE 1 and FICE 2, were again used to transform S lividans TK 23 protoplasts. In both cases transformation showed that the $Doxo^R$ character is conferred with high efficiency along with the $Ts^R$ one.

Expression of the $Doxo^R$ Character in S peucetius Mutants $Doxo^S$

The two recombinant plasmids were then introduced into some derivative mutants of S. peucetius M76 which are $Doxo^S$ (MIC 50 ug/ml). The transformants showed complementation of the $Doxo^S$ character. They could grow on doxorubicin 1500 ug/ml presenting a resistance to doxorubicin level higher than the parental strain S. peucetius M76, donor of the cloned genes (MIC 250 µg/ml). The increased level of resistance in the transformants might be explained by the high copy number of the recombinant plasmids (pIJ101 replicon, Katz et al 1983).

Restriction Enzyme Analysis of the Cloned Fragments

As the phenotype conferred by the two cloned fragments was the same, we investigated if there were one or two distinct functions able to confer the $Doxo^R$ character. FIGS. 1 and 2 show the restriction maps of the S peucetius M76-derived inserts of FICE 1 and FICE 2. Most of each map is derived from the sizes of fragments generated by single and double digests using different combinations of enzymes. The interval lengths between adjacent sites come from direct measurements of the relevant fragments in appropriate double or single digests.

There is no obvious correspondence between the maps of the two cloned fragments, suggesting that the resistance is conferred by two distinct genes.

We claim:

1. An isolated DNA molecule which is a DNA molecule having the restriction enzyme map shown in FIG. 1 or in FIG. 2, wherein said DNA molecule comprises a gene encoding doxorubicin resistance and is derived from Streptomyces peucetius.

2. A recombinant vector comprising the DNA molecule of claim 1.

3. The vector of claim 2, wherein the said vector is a plasmid.

4. The vector of claim 2, wherein the said vector is the plasmid pIJ702 in which the said DNA molecule is provided.

5. A host transformed with a vector as defined in claim 2.

6. The host of claim 5, wherein the said vector is a plasmid.

7. The host of claim 5, wherein the said vector is the plasmid pIJ702 in which the said DNA molecule is provided.

8. The host of claim 5, which is a microorganism which produces anthracyclines.

9. The host of claim 5, which is a strain of Streptomyces which produces doxorubicin.

10. The host of claim 9, which is a strain of Streptomyces peucetius.

11. A process for obtaining the DNA segment of claim 1, comprising:

(a) preparing a library of genomic DNA of Streptomyces peucetius or a strain derived therefrom;

(b) screening said library for doxorubicin resistance; and (c) obtaining an insert DNA from a recombinant vector which forms part of said library, wherein said insert has screened positive for doxorubicin resistance.

12. A process according to claim 11 which further comprises obtaining from said insert DNA a restriction fragment which contains a gene coding for doxorubicin resistance.

13. A process for the preparation of a recombinant vector comprising a gene coding for doxorubicin resistance comprising cloning the DNA molecule of claim 1 into a vector.

14. A process for the preparation of doxorubicin, which comprises culturing a strain of Streptomyces which produces doxorubicin and which has been transformed with a recombinant vector comprising the DNA molecule of claim 1, and recovering the doxorubicin thus produced.

15. The process of claim 14, wherein the vector is a plasmid.

16. The process of claim 14, wherein the said vector is the plasmid pIJ702 in which the said DNA molecule is provided.

17. The process of claim 14, wherein the said strain is a strain of Streptomyces peucetius.

* * * * *